United States Patent
Zhang et al.

(10) Patent No.: US 10,477,095 B2
(45) Date of Patent: Nov. 12, 2019

(54) SELECTING OPTIMAL IMAGE FROM MOBILE DEVICE CAPTURES

(71) Applicant: SRI International, Menlo Park, CA (US)

(72) Inventors: David Chao Zhang, Belle Mead, NJ (US); John Benjamin Southall, Philadelphia, PA (US); Michael Anthony Isnardi, Plainsboro, NJ (US); Michael Raymond Piacentino, Robbinsville, NJ (US); David Christopher Berends, Skillman, NJ (US); Girish Acharya, Redwood City, CA (US); Douglas A. Bercow, Menlo Park, CA (US); Aaron Spaulding, Menlo Park, CA (US); Sek Chai, Princeton, NJ (US)

(73) Assignee: SRI International, Menlo Park, CA (US)

( * ) Notice: Subject to any disclaimer, the term of this patent is extended or adjusted under 35 U.S.C. 154(b) by 84 days.

(21) Appl. No.: 15/573,325

(22) PCT Filed: Jan. 19, 2016

(86) PCT No.: PCT/US2016/013868
§ 371 (c)(1),
(2) Date: Nov. 10, 2017

(87) PCT Pub. No.: WO2016/182607
PCT Pub. Date: Nov. 17, 2016

(65) Prior Publication Data
US 2018/0139377 A1    May 17, 2018

Related U.S. Application Data

(60) Provisional application No. 62/222,897, filed on Sep. 24, 2015, provisional application No. 62/161,318, filed on May 14, 2015.

(51) Int. Cl.
*H04N 5/232* (2006.01)
*G06T 7/00* (2017.01)
(Continued)

(52) U.S. Cl.
CPC ....... *H04N 5/23212* (2013.01); *A61B 5/0077* (2013.01); *A61B 5/442* (2013.01);
(Continued)

(58) Field of Classification Search
CPC ... G02B 7/00; G03B 3/00; G03B 5/00; G03B 13/00
(Continued)

(56) References Cited

U.S. PATENT DOCUMENTS 5,053,798 A * 10/1991 Ohara ................. G02B 7/102
 396/135
6,201,899 B1 * 3/2001 Bergen ............... G06K 9/00134
 382/106

(Continued)

FOREIGN PATENT DOCUMENTS

| EP | 0640232 B1 | 1/1995 |
| EP | 2381390 A2 | 10/2011 |
| WO | WO9323823 A1 | 11/1993 |

OTHER PUBLICATIONS

International Search Report and Written Opinion for International Application No. PCT/US2016/013868, dated Jul. 18, 2016, 6 pages.

*Primary Examiner* — Albert Kir
(74) *Attorney, Agent, or Firm* — Hickman Palermo Becker Bingham LLP; Christine E. Orich

(57) ABSTRACT

Device logic in a mobile device configures a processor to capture a series of images, such as a video, using a consumer-grade camera, and to analyze the images to determine the best-focused image, of the series of images, that captures a region of interest. The images may be of a textured surface, (Continued)

such as facial skin of a mobile device user. The processor sets a focal length of the camera to a fixed position for collecting the images. The processor may guide the user to position the mobile device for capturing the images, using audible cues. For each image, the processor crops the image to the region of interest, extracts luminance information, and determines one or more energy levels of the luminance via a Laplacian pyramid. The energy levels may be filtered, and then are compared to energy levels of the other images to determine the best-focused image.

15 Claims, 8 Drawing Sheets

(51) Int. Cl.
  *H04N 5/235*   (2006.01)
  *G06K 9/00*   (2006.01)
  *G06K 9/03*   (2006.01)
  *G06T 7/11*   (2017.01)
  *A61B 5/00*   (2006.01)
  *G06K 9/62*   (2006.01)
  *G06T 5/20*   (2006.01)

(52) U.S. Cl.
  CPC ......... *G06K 9/00228* (2013.01); *G06K 9/036* (2013.01); *G06K 9/6212* (2013.01); *G06T 5/20* (2013.01); *G06T 7/0012* (2013.01); *G06T 7/11* (2017.01); *H04N 5/2356* (2013.01); *H04N 5/23229* (2013.01); *H04N 5/23293* (2013.01); *G06T 2207/20016* (2013.01); *G06T 2207/30088* (2013.01)

(58) Field of Classification Search
  USPC ........... 348/77, 349; 382/106, 162, 195, 275
  See application file for complete search history.

(56) References Cited

U.S. PATENT DOCUMENTS

| | | | | |
|---|---|---|---|---|
| 6,542,824 | B1* | 4/2003 | Berstis | G01C 21/16 |
| | | | | 701/472 |
| 8,724,013 | B2* | 5/2014 | Safaee-Rad | G02B 7/38 |
| | | | | 348/349 |
| 2004/0218810 | A1* | 11/2004 | Momma | A61B 5/0064 |
| | | | | 382/162 |
| 2007/0132874 | A1 | 6/2007 | Forman et al. | |
| 2009/0263028 | A1 | 10/2009 | Kwon | |
| 2009/0285504 | A1* | 11/2009 | Li | G06K 9/40 |
| | | | | 382/275 |
| 2014/0009659 | A1 | 1/2014 | Kagaya | |
| 2015/0071547 | A1* | 3/2015 | Keating | G06K 9/46 |
| | | | | 382/195 |

* cited by examiner

SELECTING OPTIMAL IMAGE FROM MOBILE DEVICE CAPTURES

CROSS-REFERENCE TO RELATED APPLICATIONS

This application claims the benefit of priority from U.S. Prov. Pat. App. Ser. Nos. 62/161,318, entitled "SURFACE METROLOGY, ILLUMINATION CONTROL, AND DIALOG-DRIVEN IMAGE CAPTURE USING A SMARTPHONE-LIKE DEVICE" and filed May 14, 2015, and 62/222,897, entitled "METHOD OF BEST CAPTURE OF CLOSE-UP IMAGES USING MOBILE PHONES" and filed Sep. 24, 2015, both of which provisional patent applications are incorporated fully herein by reference.

BACKGROUND

Ensuring health and well-being is important for life. Image processing is used more and more in health care for diagnosis and monitoring. For example, the human skin can be an indicator of an individual's well-being, in addition to being the literal face that we present to the world. Physical characteristics of the skin, such as such as the texture of one's complexion, severity and changes in a rash, bump, moles, hydration level, etc., all can provide insight into an individual's well-being. Yet, these characteristics are not yet widely utilized, as precise measurement typically requires specialized custom built imaging system or a visit to an expert. The specialized systems are expensive and bulky, as they need to operate under controlled lighting, appropriate camera angle, and proper distance from the object of interest. Visiting an expert's office is time consuming and costly. Neither of these approaches lends itself to personal daily use.

It is very attractive to use the cell phone to capture these images and provide the same functions of feature identification, e.g., for cosmetics guidance, diagnostics, or product identification. However, the cell phone is hand-held and human hands are shaky; the captured static image is often blurred and out of focus. Further, a subject photographing his own face cannot see the facial skin image at the time the image is taken, and therefore cannot determine if the camera is properly oriented and the image is in focus.

BRIEF DESCRIPTION OF DRAWINGS

This disclosure is illustrated by way of example and not by way of limitation in the accompanying figures. The figures may, alone or in combination, illustrate one or more embodiments of the disclosure. Elements illustrated in the figures are not necessarily drawn to scale. Reference labels may be repeated among the figures to indicate corresponding or analogous elements.

DETAILED DESCRIPTION

Figure 1:
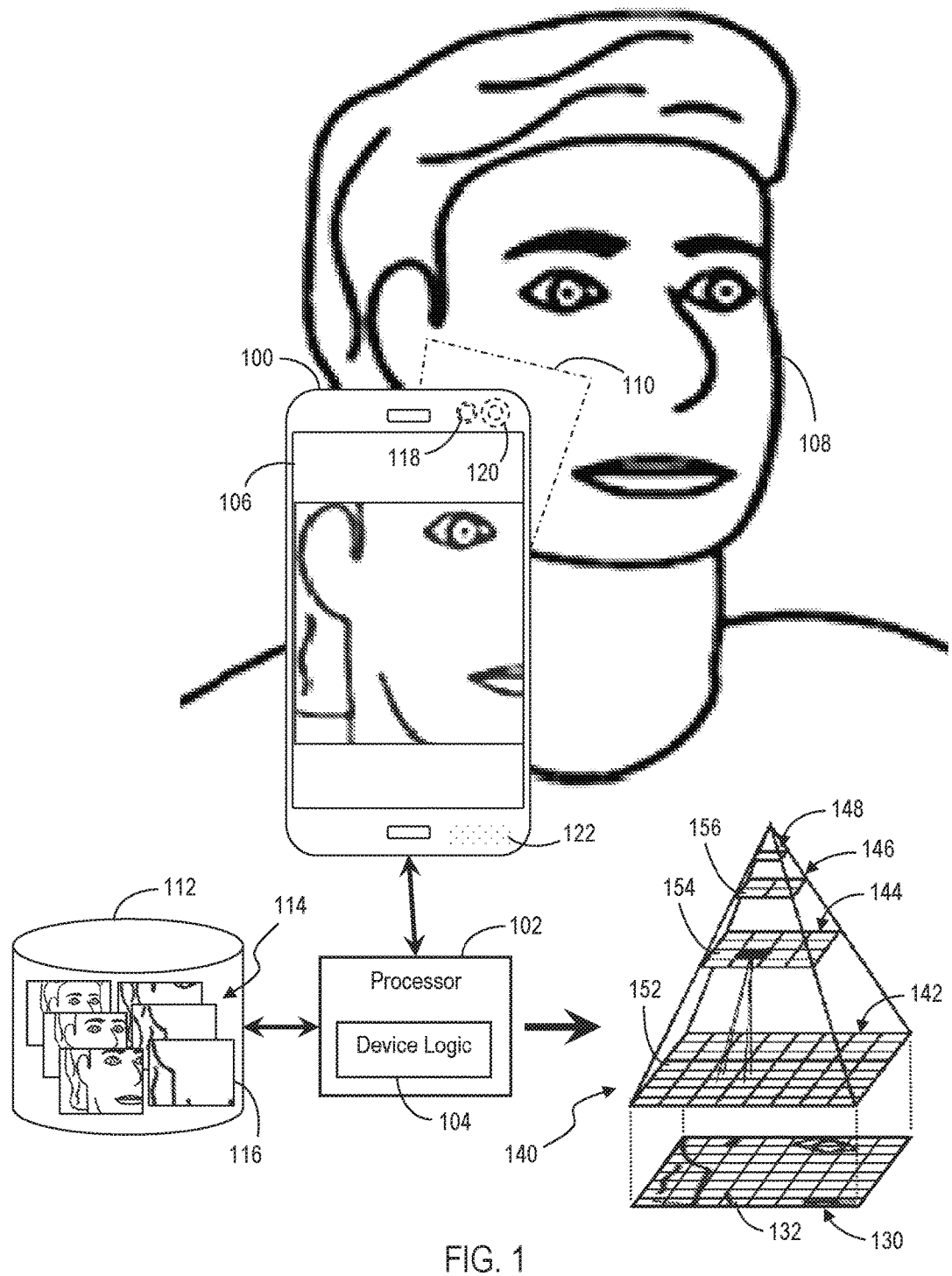
FIG. 1 is a diagram of an example system configured to identify a best-focused digital photograph from a plurality of digital photographs captured by a mobile device camera.

While the concepts of the present disclosure are susceptible to various modifications and alternative forms, specific embodiments thereof are shown by way of example in the drawings and are described in detail below. It should be understood that there is no intent to limit the concepts of the present disclosure to the particular forms disclosed. On the contrary, the intent is to cover all modifications, equivalents, and alternatives consistent with the present disclosure and the appended claims.

The present disclosure provides systems, device configurations, and processes for using a smartphone or other mobile device with a consumer-grade camera to determine, from a video or a series of digital photos, a best-focused image of a textured surface or other region of interest. While high in resolution, images produced by consumer-grade cameras have limited quality due to the selection of cost-effective lenses, image sensors, processing hardware, and other electronic components. Images are often out of focus, even when the corresponding photograph is captured at the proper focal length. Images can contain capture and/or processing artifacts such as additive white Gaussian noise, spectral highlights, and other anomalies that occupy some or all spatial frequencies of the image, which confuses and degrades the operation of known focus detection methods. Embodiments herein describe applying a pyramidal transform to an image, determining the Laplacian energies of the levels in the resulting Laplacian pyramid, and determining properties such as focus and noise content of the image from ratios between the Laplacian energies. The best-focused image of a series of related images can then be determined by comparing the Laplacian energy properties of the images on a rolling basis.

Referring to FIG. 1, a mobile device 100 adapted for performing the present image identification processes may be a laptop computer, tablet computer, e-reader, smartphone, personal data assistant, or other mobile device; in other embodiments, the present systems and processes may be implemented in an immobile or less-mobile computing device such as a personal computer, set-top box, digital media player, microconsole, home automation systems, or other computing device. The mobile device 100 may include a processor 102, which may be a central processing unit (CPU), microprocessor, or other suitable processor that can control a camera 120 and employ various components of the mobile device 100 to enable capture of a plurality of photographs of the region of interest 110 and store them temporarily as a plurality of images 114 (i.e., image files) in a data store 112. As used herein, a data store may be any repository of information that is or can be made freely or securely accessible by the mobile device 100. Suitable data stores include, without limitation: databases or database systems, which may be a local database, online database, desktop database, server-side database, relational database, hierarchical database, network database, object database, object-relational database, associative database, concept-oriented database, entity-attribute-value database, multi-dimensional database, semi-structured database, star schema database, XML database, file, collection of files, spreadsheet, or other means of data storage located on a computer, client, server, combination of any number of servers, or any other data storage device and/or data storage media, in any standard, distributed, virtual, or clustered environment known in the art or developed in the future; file systems; and electronic files such as web pages, spreadsheets, and documents. An image file has a filename and contains data representing an image, and may contain other data as well, such as a time, a date, and a location of capture, a device used to capture, settings of the capture device at the time the image was captured, an image histogram, and the like.

The processor 102 executes device logic 104 in the processor 102 or in memory of the device 100 to process the plurality of images 114, and further, in some embodiments, to aid a user of the mobile device 100 to position, move, and otherwise control the mobile device 100 so that the plurality of images 114 include the region of interest 110 and at least the best-focused captured image 116 is of a desired quality. In one example of aiding the user, the user may be the subject 108 himself, and the region of interest 110 may be the skin of the subject's 108 cheek, as illustrated. In this case, whether the camera 120 is on the same side of the mobile device 100 as the display screen 106, or on the opposite side, the subject 108 cannot see the display 106 during image capture. The processor 102 may send audible cues to the subject 108 via a speaker 122 or another output device; such audible cues can include alerts and/or speech providing guidance such as, without limitation, informing that the region of interest 110 is not in the camera 120 field of view, informing that the subject 108 is moving the mobile device 100 too fast or too slow, informing that the camera is tilted too much with respect to the skin surface, informing that the ambient light level is too low, or indicating that a best-focused image has been captured and identified.

The mobile device 100 may include one or more cameras 120, which may be any suitable image capture device that can be integrated in or connected to the mobile device 100. While cameras 120 of any level of quality and/or sophistication may be used, including digital single-lens reflex cameras and mirrorless system cameras, the processes described below are particularly configurable to be applied in consumer-grade smartphone (e.g., APPLE IPHONE, SAMSUNG GALAXY, etc.) and tablet (e.g., APPLE IPAD, AMAZON KINDLE FIRE, etc.) environments, wherein consumer-grade cameras 120 are nearly universally installed. Exemplary embodiments are described in which the focal length of the camera 120 may be fixed during image capture. Some consumer-grade cameras do not have adjustable lenses that provide a range of focal lengths; the present approaches are suited for such devices. Most current smartphones, however, are not only equipped with adjustable lenses, but also employ autofocus motors and/or software operating in conjunction with a range sensor to move the lens and simplify photography. Unfortunately, autofocus algorithms are not tuned to acquire the finest-detailed close-up images of textured surfaces such as skin. The present approaches operate on such devices by disabling or deactivating autofocus and fixing the focal length at an optimal position.

In some embodiments, the mobile device 100 may advantageously capture the plurality of images 114 sequentially (i.e., in a chronological sequence or order), as a video comprising frames that are the plurality of images, or using a native rapid-acquisition mode such as burst or continuous high-speed shooting mode, or from repeated manual actuation of a camera shutter, or using another camera control algorithm described herein. The plurality of images 114 may be captured as a user is moving the mobile device 100, either intentionally on a path or accidentally such as by dropping or shaking the mobile device 100. Components such as range finders, accelerometers, and other sensors, camera flashes 118 and other lights, display screens 106, global positioning systems, network connections, and software modules such as image recognition applications, may all be employed to guide positioning and movement of the mobile device 100, activation of the shutter, illumination of the subject 108, and the like.

The systems, devices, and methods are described as operating on a plurality of images 114 that are strongly and clearly related, such that the best-focused image 116 will be stored and/or acted upon, and the others expectedly disposed of. Examples include series of images that are related in both time and subject matter as described above, as well as images taken of the same subject but at different times, such as before and after photographs of treated skin. Processes are described below for re-capturing images when the plurality of images 114 are not sufficiently related, or when even the best-focused image 116 is still blurry. Presuming a successful capture of a plurality of related images 114, the processes for identifying the best-focused image 116 are now described with further reference to the figures.

Referring again to FIG. 1, the processor 102 makes determinations regarding the focus of an image 130 based on pixel data of some or all of the pixels 132 of the image 130. In particular, the processor 102 applies a discrete Laplace operator iteratively to the image 130, forming what is known as a Laplacian pyramid. The discrete Laplace operator is a well-established mathematical operation that transforms a first function of a real variable, such as space, into a second function such as spatial frequency. The Laplacian pyramid representation has known applications in image processing, including edge detection, blurring, and sharpening; a processor convolves the image with one or more filtered versions of the image produced by the discrete Laplace operator to perform these tasks. A Laplacian pyramid, for image processing, may be considered a spatial bandpass or high-pass representation that transforms the image from the spatial domain to the spatial frequency domain. The Laplacian pyramidal transform uses a kernel (the discrete Laplace operator) to control its output, the kernel having parameters including a filter size (a two-dimensional matrix wherein the elements represent pixels, the kernel giving weights to the pixel being filtered and its adjacent pixels within the kernel area), a cutoff frequency, and, optionally, a number of iterations. Typically, the Laplacian pyramidal transform operates on a grayscale version of the image 130, using only the luminance of each pixel 132; thus, the spatial frequency components of the Laplacian pyramidal transform pertain to the brightness of areas of the image 130.

Applying the discrete Laplace operator iteratively to the image 130 generates a Laplacian pyramid 140 having one or more levels. The levels contain spatial frequency information for areas of the image 130. The spatial frequency information represents an amount that the luminance of the image 130 varies over a distance set by the filter size. A first level 142 of the pyramid 140 (referred to as L0 commonly and herein) contains a luminance value 152 for each pixel 132 of the image 130. The luminance value 152 represents a frequency of the luminance of the corresponding pixel 132 in light of the Laplacian pyramid parameters—that is, the spatial frequency is calculated across the pixels 132 within the filter matrix, the pixel 132 being filtered placed at the center of the matrix, and the spatial frequency is filtered out if it does not exceed the cutoff frequency. To illustrate the pyramid 140, the first level 142 can be convolved back to the spatial domain, where it is represented by a high-pass filtered image of the same size as the original image 130; the luminance values 152 correspond to the luminance of the pixels in the high-pass filtered image.

The discrete Laplace operator computes a spatial derivative of each level to produce the next level in the pyramid 140, reducing the size (i.e., the number of luminance values) in each subsequent level by half. Thus, a plurality of first luminance values 152 of the first level 142 are downsampled into one second luminance value 154 of the second level 144 (referred to as L1 commonly and herein), a plurality of second luminance values 154 are downsampled into one third luminance value 156 of the third level 146 (referred to as L2 commonly and herein), and so on until a top level 148 is produced and contains just one luminance value. The frequencies filtered out between levels are modified by the derivative, such that each "distance" between levels corresponds to a spatial bandpass filter, the width of each frequency band depending on the resolution of the image. The number of levels 142-148 may be limited by setting a maximum number of iterations of the Laplacian pyramid. The processor 102 uses the corresponding luminance values of one or more of the levels to derive the focus information.

Figure 2:
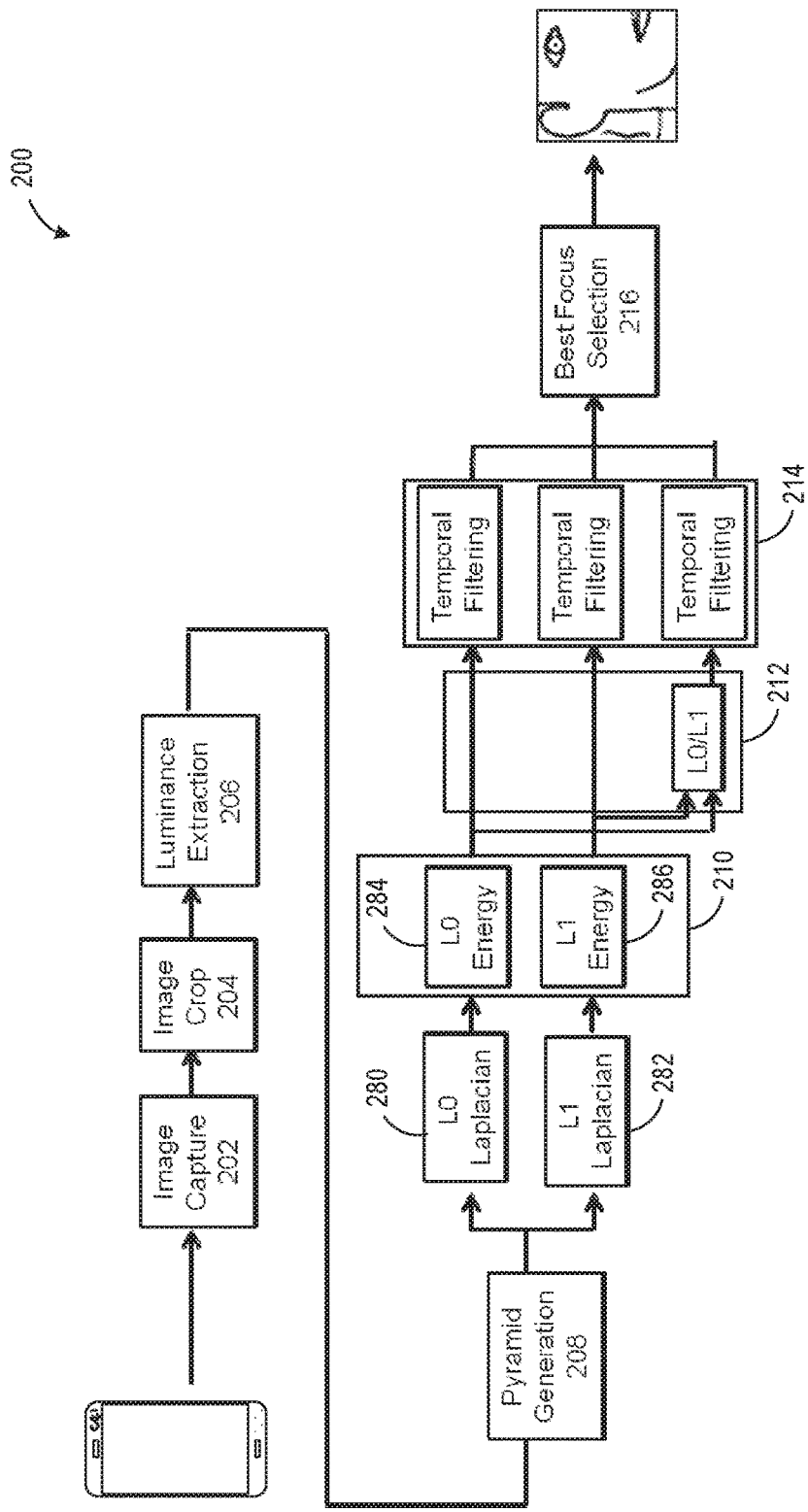
FIG. 2 is a diagram of an exemplary progression of image processing stages executed by a processor in accordance with the present disclosure.

Referring to FIG. 2, a processor of the mobile device may execute device logic, including program instructions, software modules, hardware interfaces, and the like, to execute the image processing in a progression 200 of stages. The image capture stage 202 includes receiving one or more of the plurality of images to be compared, the images captured by the camera of the mobile device. In other embodiments, the images may be captured by multiple devices and sent to the processor. Various techniques for controlling the camera to capture the proper images are described below. In particular, at stage 202 the processor may fix the focal length of the camera before the images are captured. In some embodiments, the processor may receive all of the plurality of images at once and process them through the progression 200 accordingly. In other embodiments, the processor may receive each image as it is captured, and may process the image through the progression 200 immediately, even while subsequent images are still being captured and/or received.

The image crop stage 204 includes cropping the image to a reduced size. The size may be selected to make the images uniform. The crop may be to a uniform or non-uniform size and the crop region may be located over the region of interest in the image. Cropping may be performed in the center of the image, or may be offset spatially as determined by other factors, such as degree of brightness, hue, specularity or saturated values in the captured image. The image crop stage 204 may further include rotating the image and/or performing other image modifications.

The luminance extraction stage 206 includes converting the color image to a grayscale image for processing by the Laplacian pyramid. Only the luminances of the pixels in the image are needed. Any suitable conversion technique may be used to preserve the luminance and remove the color in the image. For example, the image may be represented by a luminance channel and a chrominance channel, with channel information derived for each pixel from the pixel's RGB value, and the processor may extract the luminance channel to create a new grayscale image.

The pyramid generation stage 208 includes transforming the grayscale image, using an iterative discrete Laplace operator, to produce a Laplacian pyramid for the image, the pyramid including at least a first level based on the grayscale image and a second level based on the first level, as described above. In an exemplary embodiment, the discrete Laplace operator uses a five-pixel by five-pixel matrix as the filter size. This filter size produces a reasonable compromise between computational efficiency and sharpness of bandpass cutoff frequency; other filter sizes may be used. Applying the discrete Laplace operator thus produces a plurality of first luminance values (i.e., L0 Laplacian values 280) from the grayscale image and a plurality of second luminance values (i.e., L1 Laplacian values 282) from the plurality of first luminance values.

The energy calculation stage 210 includes determining energy values representing the Laplacian energy of each level (i.e., a first energy value 284 for L0 and a second energy value 286 for L1) of the pyramid. The Laplacian energy is a measurement of the frequency response across the entire level (i.e., within the frequency band represented by the level): Laplacian energy is relatively high when spatial frequency components in the original luminance image have large amplitudes within the bandpass region of the level, which in turn correspond to large luminance variations in the corresponding area of the transformed image. In some embodiments, the energy value of a level is determined by computing the square of each luminance value, and then computing the mean/average of the intermediate (i.e., squared) values to produce the energy value.

The energy values can be used directly to select focused images. For example, in a plurality of images, the image wherein all of the energy values are at their peak values may have the best focus. However, this approach is locally myopic: even though the energy values are peaking, the energy value of one of the levels may be significantly higher than the others. This is particularly shown in images of a skin surface that exhibits "weak" features. Weak features are features that, in the image, are not significantly differentiated from the base appearance of the skin and/or from other features; that is, the base appearance of the skin forms a "background" color and texture of the image, and the weak features, such as wrinkles, furrows, pores, slight imperfections, and the like, do not stand out from the background. The images, including blurred images, of weak features may be dominated by image noise, such as additive white Gaussian noise, which is recorded as frequency variations in L0 but filtered out in subsequent levels. Correspondingly, the energy value of L0 is significantly higher than the energy value of L1. If the images are being processed as they are captured, a local peak of the L0 and L1 energy values can identify a blurred image as the best-focused image, when the best-focused image has actually not yet been captured.

A threshold comparison stage 212 accounts for such false identifications. The processor determines whether the energy values are above an energy threshold set to eliminate images that are too blurry. The processor also determines whether a ratio of the L0 energy value to the L1 energy value is approximately 1.0, i.e., the energy values are approximately equal. A range around 1.0 may be used to determine the extent of "approximately" equal. In one example, the ratio must be at least 0.5 and at most 1.9 to be considered approximately 1.0. The range may depend on the characteristics of the camera, such as focal length, image resolution, shutter speed, capture rate, etc. If the image meets these conditions, the processor may retain the image and its energy values for further processing; in various embodiments, the processor may also retain the images that do not meet the thresholds and their energy values, or just their energy values, or may discard such images and energy values.

These conditions may correspond to a global best-focused image, because the energy values reach their peak when there is the most frequency content (i.e., the image is sharpest), and the image is not dominated by noise when the energy values are approximately equal. In contrast, a near-blurred image, captured when the mobile device is separated from the subject by a distance that is less than the focal length, has a relatively high ratio because the L0 energy value is much higher than the L1 energy value; a far-blurred image, captured when the mobile device is separated from the subject by a distance that is greater than the focal length, has energy values that quickly fall below the energy threshold. Thus, in some embodiments, the processor may identify all of the "valid" images in the plurality of images by determining that the valid images have a first (i.e., L0) energy value that exceeds the energy threshold and is approximately equal to the image's second (i.e., L1) energy value. The processor may then identify the valid image with the highest first energy value as the best-focused image.

Referring again to FIG. 2, the illustrated embodiment may account for continuously received images in the plurality of images in a temporal filtering stage 214. This stage 214 may calculate a rolling or moving average across a predetermined number of the most recently received frames (i.e., images), such as by applying a boxcar filter across the last three received images—the current (i.e., last-received) image, a first previous image occurring in the image sequence immediately before the current image, and a second previous image occurring in the image sequence immediately before the previous image (alternatively, these images may be referred to as a first image, a previous image occurring in the image sequence immediately before the first image, and a subsequent image occurring in the image sequence immediately after the first image). The temporal filtering stage 214 may extend the threshold comparison of the previous stage 212 to apply to an average of the values of the images in the boxcar filter.

Thus, the processor may calculate an average first energy value from the first energy values of the current, first previous, and second previous images, and may calculate an average second energy value from the second energy values of the current, first previous, and second previous images. The processor determines whether the average energy values are above the energy threshold and are approximately equal (i.e., the ratio of the average first energy value to the average second energy value is approximately 1.0). If so, the processor may add the first previous image (which is at the center of the boxcar filter—note that the current image has no subsequent image yet) and the average energy values to a queue for valid images whose average energy values meet the thresholds. The queue may have its sequence, which takes the image order of the plurality of images but removes the images that are determined to not be valid. The queue may also have a minimum queue size corresponding to the number of images that the processor must identify as valid before it can proceed to the next stage 216.

The best focus selection stage 216 includes determining the best-focused image of the plurality of images from the valid images in the queue. In one embodiment, such as when the camera has stopped capturing the plurality of images, the processor may select the valid image with the highest average first energy value as the best-focused image. In another embodiment, the camera may still be capturing images for processing, yet the best-focused image may be determined: the processor may determine whether any of the valid images has an average first energy value that is higher than those of the images immediately before and immediately after the valid image in the queue. If so, the processor may select that valid image as the best-focused image. Furthermore, the processor may control the camera to stop capturing the plurality of images.

The best-focused image is thus selected, and the processor may perform one or more actions associated with the best-focused image. Non-limiting examples include terminating image capture, deleting the video or all other images of the plurality of images, providing an alert or indicator to the user or to another device that the best-focused image has been obtained, presenting the best-focused image on the display of the mobile device, storing the best-focused image or sending it to a remote device for storage or processing, and the like. The actions may include processing the image according to a particular desired application. For example, where the images are of a skin surface, the best-focused image may be used in a cosmetic, dermatological, or other aesthetic or medical application. Such applications include determining conditions of the skin. In one embodiment, the processor may execute additional device logic to analyze skin features in the image. Non-limiting examples of the analysis include: determining a skin moisture content, skin texture, or skin color; identifying the presence or absence of acne or rosacea; comparing the image to previously captured images to estimate treatment progress, wound healing, advancement of wrinkles and/or furrows, color changes, and the like. Other suitable applications in which a best-focused image of a mobile device may be acted upon include image sensing, applied physics applications, robotics applications, and other application in which finely detailed, close-up images of a textured surface are used.

Figure 3:
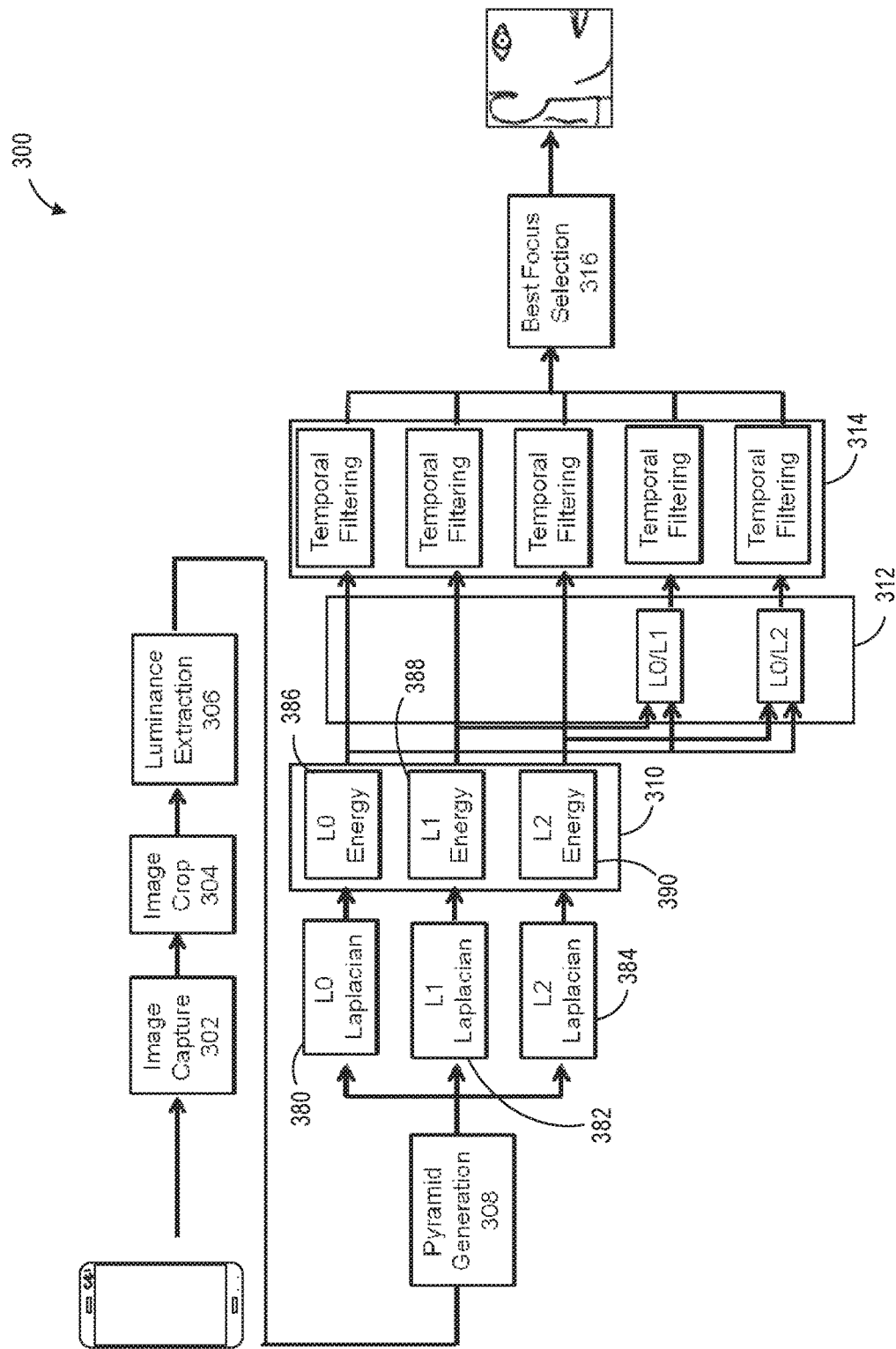
FIG. 3 is a diagram of another exemplary progression of image processing stages executed by a processor in accordance with the present disclosure.

FIG. 3 illustrates another embodiment of executing the image processing in a progression 300 of stages. The processor follows the progression 300 to utilize an additional level of the Laplacian pyramid, which adds complexity and thus processing time and resource overhead, but may more accurately produce the best-focused image when compared to the progression 200 of FIG. 2. The image capture stage 302, image cropping stage 304, and luminance extraction stage 306 proceed as described above with respect to stages 202-206 of FIG. 2. At the pyramid generation stage 308, the processor applies the discrete Laplace operator described above with respect to stage 208 to generate a Laplacian pyramid for the greyscale image. The Laplacian pyramid includes at least a first level based on the grayscale image, a second level based on the first level, and a third level based on the second level. As in stage 208, the levels have corresponding pluralities of luminance values representing the Laplacian values of the corresponding levels (i.e., L0 Laplacian values 380, L1 Laplacian values 382, and L2 Laplacian values 384).

The energy calculation stage 310 includes determining energy values representing the Laplacian energy of each level (i.e., a first energy value 386 for L0, a second energy value 388 for L1, and a third energy value 390 for L2) of the pyramid. Again, the energy values 386-390 can be used directly to select focused images. With respect to the weak features described above, the L2 energy value behaves similarly to the L2 energy value, being dominated by the energy value of L0 in near-blurred images, and quickly dropping below the energy threshold in far-blurred images.

A threshold comparison stage 312 includes determining whether the energy values are above the energy threshold. The processor also determines whether a ratio of the L0 energy value to the L1 energy value and a ratio of the L0 energy value to the L2 energy value are each approximately 1.0, i.e., the energy values are approximately equal. A temporal filtering stage 314 may include calculating a rolling or moving average across a predetermined number of the most recently received frames (i.e., images). The processor may calculate an average first energy value from the first energy values of the current, first previous, and second previous images, an average second energy value from the second energy values of the current, first previous, and second previous images, and an average third energy value from the third energy values of the current, first previous, and second previous images. The processor determines whether the average energy values are above the energy threshold and are approximately equal (i.e., the ratios of the average first energy value to the average second energy value and to the average third energy value are approximately 1.0). If so, the processor may add the first previous image and the average first energy value to a queue for valid images whose average energy values meet the thresholds, as described above.

Figure 4:
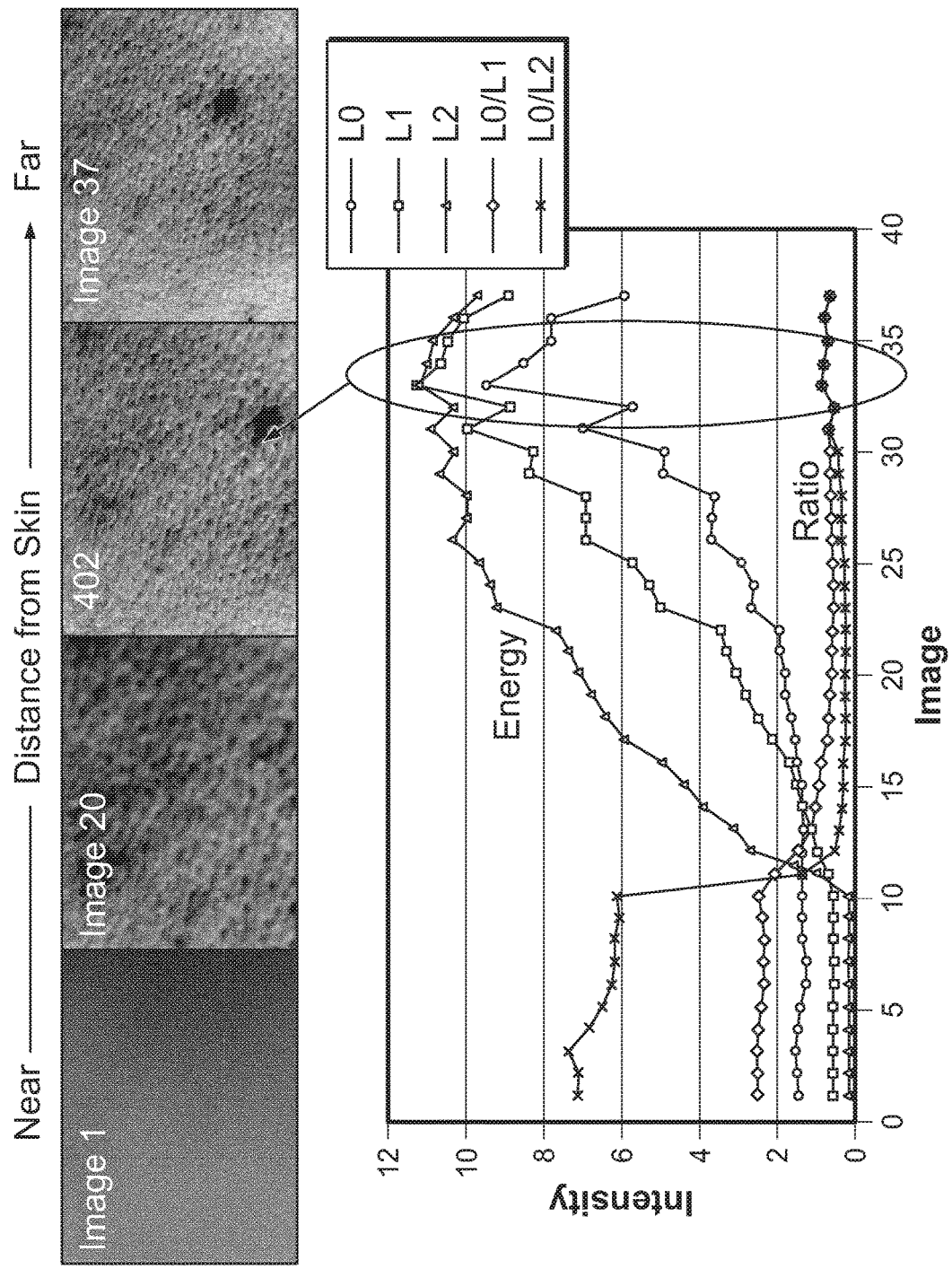
FIG. 4 is a graph plotting computed energy values and ratios thereof for a series of images, in accordance with the present disclosure.
Figure 5:
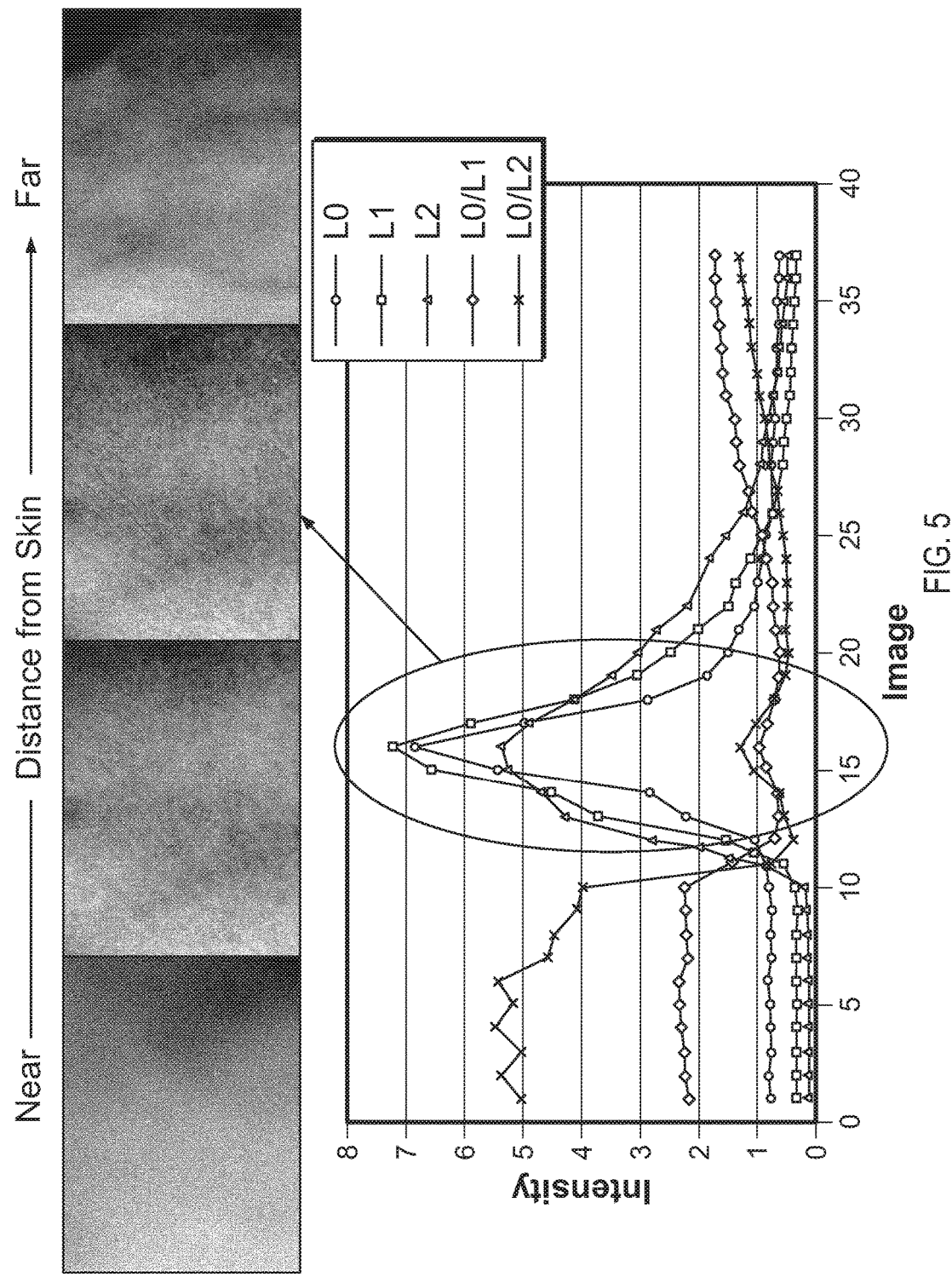
FIG. 5 is a graph plotting computed energy values and ratios thereof for another series of images, in accordance with the present disclosure.

The best focus selection stage 316 proceeds as described above with respect to stage 216 of FIG. 2. The accuracy may be improved over the faster progression 200 of FIG. 2 due to the additional check of the energy and ratio corresponding to the third level of the Laplacian pyramid. FIGS. 4 and 5 plot the energy values and ratios for two exemplary image captures, in which the camera was moved from near the skin to far from the skin as 37 images were captured. The plots demonstrate that the energy values of L0, L1, and L2 peak for the sharpest images 402, 502, while the ratios L0/L1 and L0/L2 remain at approximately 1.0. The plots also demonstrate the dominance of the L0 energy when the camera is very close to the subject.

Figure 6:
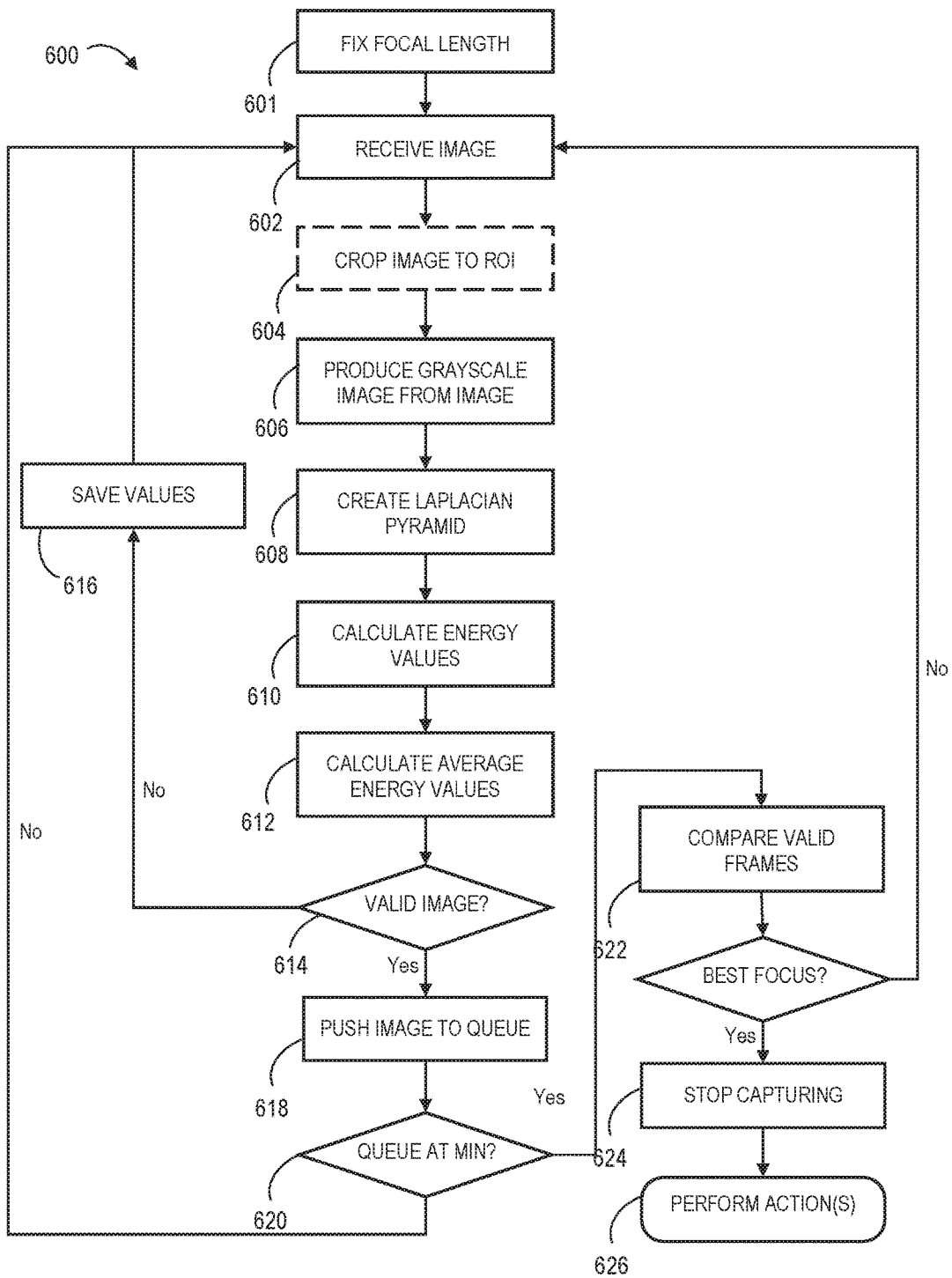
FIG. 6 is a flowchart of an exemplary method of determining a best-focused image from a plurality of images, in accordance with the present disclosure.

The correlative rising, peaking, and falling of the energy values, like those shown in the plots, correspond to the mobile device approaching and then passing a distance from the subject that is equal to the fixed focal length of the camera. FIG. 6 illustrates a method 600 of determining the best-focused image when the plurality of images is captured automatically as the mobile device is moved from a point within the focal distance from the subject to a point outside the focal distance from the subject. At step 601, the processor may set the focal length of the camera to a fixed position. Advantageously, the fixed position may be a minimum focal length achievable by the camera, as this ensures that the best-focus image captures the finest details of the surface. At step 602, the processor may receive one of the plurality of images. Receiving the image may comprise controlling the camera to capture the image. The processor may initiate the capture upon receiving an input signal, such as a user input actuating the shutter, a signal from a range sensor or accelerometer, or another input. The processor may control the camera to capture an image at a constant capture rate, such as a number (e.g., 5-15) of frames per second, and thus may automatically actuate the next capture according to a system clock.

At step 604, the processor may, optionally, crop the image to a range of interest or to a desired size. At step 606, the processor may produce a grayscale image from the cropped image. At step 608, the processor may apply the Laplacian operator iteratively to the grayscale image to produce the luminance values of the Laplacian pyramid as described above. At step 610, the processor may calculate the energy value for each relevant level of the Laplacian pyramid. At step 612, the processor may calculate the average energy values for the immediately previous image, or for the current image if there is no previous image, across the current image and one or more previous images, if any. At step 614, the processor may determine whether the previous image is a valid image, i.e., that the previous image's average energy values exceed the energy threshold and are approximately equal. If not, at step 616 the processor may save the energy values for the image and return to step 602 to capture the next image.

If the previous image is a valid image (step 614), at step 618 the processor may push the previous image to the valid image queue. At step 620, the processor determines whether a minimum number of valid images are in the queue. If not, the processor returns to step 602 to capture the next image. If so, at step 622 the processor compares the average first energy value of one or more of the valid frames to the corresponding average first energy values of the immediately previous and immediately subsequent valid images in the queue. The processor may do this for all of the valid images, or only for some, or only for the valid image immediately previous to the previous image in the queue. If the comparison (step 622) does not yield a best-focused image (i.e., a valid image with an average first energy value higher than those of the immediately previous and immediately subsequent valid images in the queue), the processor returns to step 602 to capture the next image. If a best-focused image is determined, at step 624 the processor controls the camera to stop capturing the plurality of images, and at step 626 may perform additional actions associated with the best-focused image.

Various steps of the best-focus determination processes, such as method 600, may include substeps or companion steps in which the processor controls components of the mobile device to interact with the user in order to facilitate the processes. For example, the processor may, at step 602, instruct the camera to capture the plurality of images for 4.5 seconds at a capture rate of 8 images per second. During the automated capture, the processor may receive a signal from an accelerometer of the mobile device, and may determine from the signal that the user is moving the mobile device too fast. The processor may generate an audible, visual, or tactile cue to alert the user to slow down.

To interact with the user, the mobile device may implement a virtual personal assistant (VPA) that is configured to perform domain-specific tasks relevant to the capture and processing of the best-focused image. Among others, a suitable VPA architecture that may be implemented on the mobile device and configured to operate in the domain is the generic virtual assistant platform described in U.S. Pat. No. 9,082,402, owned by the present applicant and incorporated fully herein by reference to the extent permitted. The generic virtual assistant platform may receive a plug-in comprising at least a domain-specific language model and a domain-specific task flow. The language model may provide a vocabulary that is relevant to communicating the necessary actions to the user and understanding the user's inquiries and responses in a conversational natural language (e.g., speech-based) manner. The task flow identifies domain-specific actions to be taken or initiated by the computing device, such as identifying the points in the focus determination process when the processor will have to generate a cue for the user or receive an input from the user, as well as the points when the processor should survey components, operations, or data to determine whether interaction with the user is needed.

Figure 7:
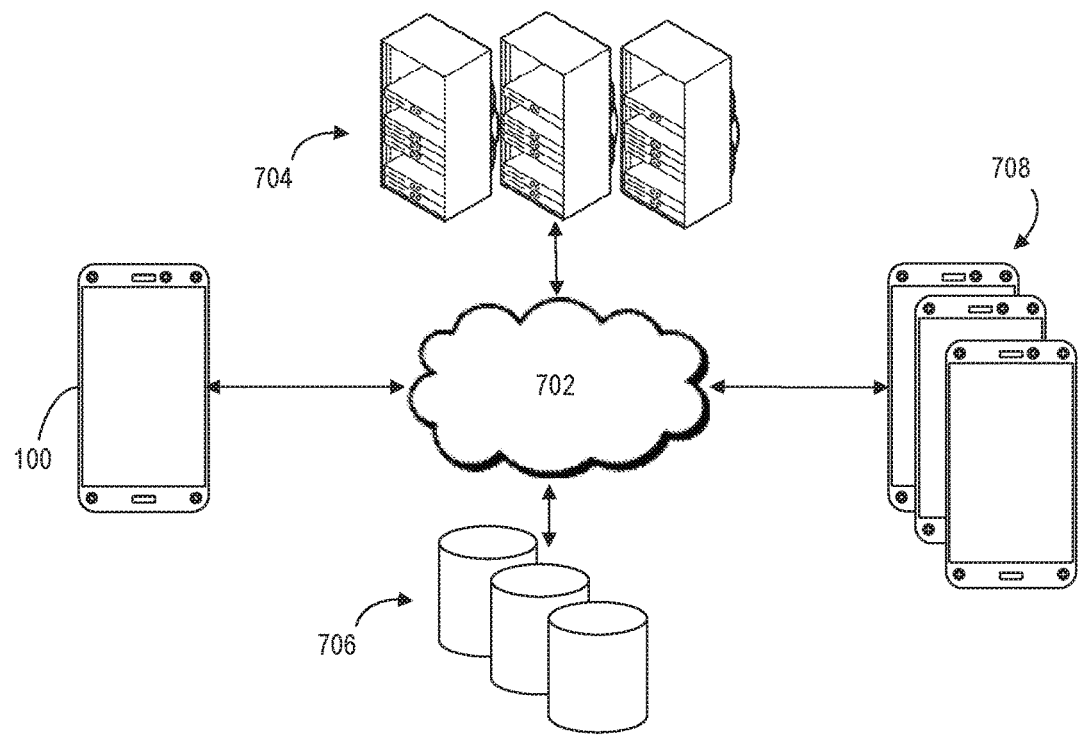
FIG. 7 is a diagram of a communication network in accordance with the present disclosure.

The VPA may advantageously be available at all times. The VPA is directly operated by the user and, in some embodiments, does not require any external support, thus ensuring a high degree of privacy. Referring to FIG. 7, while a local environment completely physically contained on the computing device 100 may be used, different distributed environments may also be used, as appropriate, to implement various embodiments. To facilitate operation of the VPA, the mobile device 100 may communicate with remote devices via a communication network 702. The network 702 can include any appropriate network, including an intranet, the Internet, a cellular network, a local area network, a satellite network or any other network and/or combination thereof. Components used for such a system can depend at least in part upon the type of network and/or environment selected. Protocols and components for communicating via such a network 702 are well known and will not be discussed in detail. Communication over the network 702 can be enabled by wired or wireless connections and combinations thereof. The communication network 702 may facilitate completion of tasks by providing a connection to servers 704 and data stores 706 that are remote from the computing device 100. Additionally, the communication network 702 may facilitate receipt by the computing device 100 of messages or other VPA data from the other user devices 708 and/or servers 704, as well as transmission from the computing device 100 of responses to messages, etc.

The mobile device 100 may communicate with one or more servers 704 to send and receive VPA data, such as updates to the language model and/or task flow. In particular, one or more of the servers 704 may be configured to parse and generate speech, and the mobile device 100 may send input audio and/or generated cues to the servers 704 for translation. The mobile device 100 may also directly access one or more remote data stores 706 to store and retrieve VPA data. One or more other user devices 708 may also communicate via the communication network 702, and may share data that improves VPA operation with the mobile device 100, the servers 704, and/or the data stores 706.

There may one server 704 or several cooperating servers 704 of homogenous or varying types, layers or other elements, processes or components, which may be chained or otherwise configured, which can interact with each other and with the mobile device 100 to perform tasks such as obtaining data from an appropriate data store 706 that is accessible locally to the cooperating server 704 or remotely over the network 702. Servers, as used, may be implemented in various ways, such as hardware devices or virtual computer systems. In some contexts, servers may refer to a programming module being executed on a computer system. The servers 704 can include any appropriate hardware, software and firmware for integrating with the data store as needed to execute aspects of one or more applications for the client device, handling some or all of the data access and business logic for an application. The servers 704 may provide access control services in cooperation with the data stores 706 and are able to generate content including, text, graphics, audio, video and/or other content usable to be provided to the user, which may be served to the mobile device 100 in any suitable format, including HyperText Markup Language ("HTML"), Extensible Markup Language ("XML"), JavaScript, Cascading Style Sheets ("CSS"), or another appropriate client-side structured language. Content transferred to the mobile device 100 may be processed by the mobile device 100 to provide the content in one or more forms including, forms that are perceptible to the user audibly, visually and/or through other senses including touch, taste, and/or smell. The handling of all requests and responses, as well as the delivery of content between the computing device 100 and the servers 704, can be handled by one of the servers 704, such as a web server using PHP: Hypertext Preprocessor ("PHP"), Python, Ruby, Perl, Java, HTML, XML, or another appropriate server-side structured language in this example. It should be understood that the cooperating servers 1604 are not required and are merely example components, as structured code discussed can be executed on any appropriate device or host machine as discussed elsewhere. Further, operations described as being performed by a single device may, unless otherwise clear from context, be performed collectively by multiple devices, which may form a distributed and/or virtual system.

The data stores 706 can include several separate data tables, databases, data documents, dynamic data storage schemes and/or other data storage mechanisms and media for storing data relating to a particular aspect of the present disclosure, including without limitation the VPA data and the image data. It should be understood that there can be many aspects that may need to be stored in the data store, such as user information and access rights information, which can be stored in any appropriate mechanisms in the data stores 706. The data stores 706 may be operable, through logic associated therewith, to receive instructions from the servers 704 and obtain, update, or otherwise process data in response thereto. The servers 704 may provide static, dynamic or a combination of static and dynamic data in response to the received instructions. Dynamic data, such as data used in web logs (blogs), shopping applications, news services and other applications may be generated by server-side structured languages as described or may be provided by a content management system ("CMS") operating on, or under the control of, the servers 704.

Each server 704 typically will include an operating system that provides executable program instructions for the general administration and operation of that server and typically will include a computer-readable storage medium (e.g., a hard disk, random access memory, read only memory, etc.) storing instructions that, when executed by a processor of the server, allow the server to perform its intended functions. Suitable implementations for the operating system and general functionality of the servers are known or commercially available and are readily implemented by persons having ordinary skill in the art, particularly in light of the disclosure. The environment, in one embodiment, is a distributed and/or virtual computing environment utilizing several computer systems and components that are interconnected via communication links, using one or more computer networks or direct connections. However, it will be appreciated by those of ordinary skill in the art that such a system could operate equally well in a system having fewer or a greater number of components than are illustrated in FIG. 7. Thus, the depiction in FIG. 7 should be taken as being illustrative in nature and not limiting to the scope of the disclosure.

Figure 8:
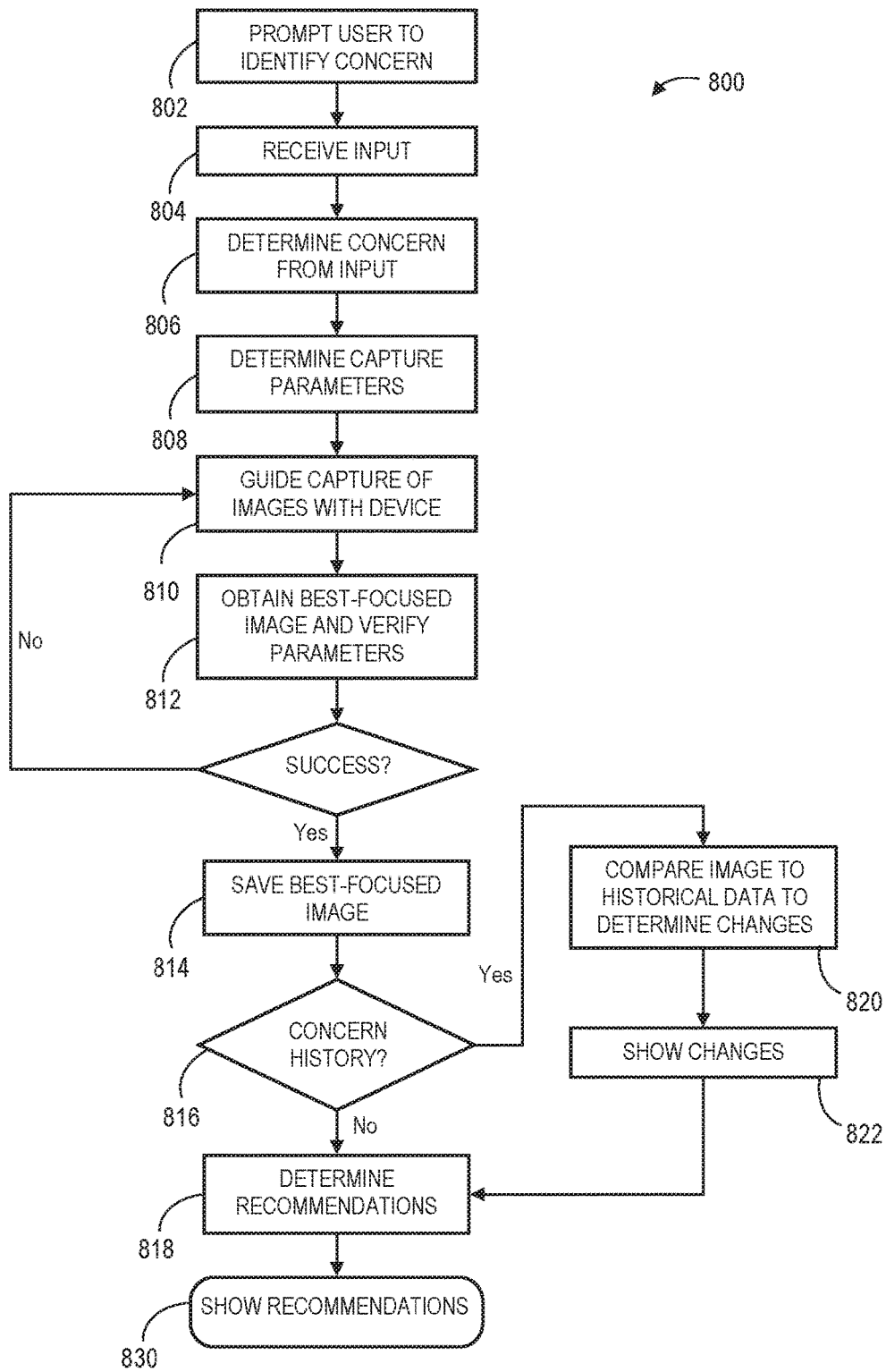
FIG. 8 is a flowchart of an exemplary method of analyzing a user concern using a virtual personal assistant, in accordance with the present disclosure.

Referring to FIG. 8, a VPA implemented on the user device may perform a method 800 of helping the user analyze a health concern, such as a skin condition. The method 800 may be adapted, using the domain-specific modules of the VPA, to analyze any physical surface that can be photographed using the mobile device and the processes described herein. At step 802, the VPA may prompt the user, using audible and/or visual cues from the mobile device, to enter input identifying the user's concern. At step 804, the VPA may receive the input from the user, and at step 806 the VPA may determine the identified concern from the user input. In some embodiments, the VPA may determine the concern using one or a combination of inputs relating to biological and treatment information for the user, such as a set of symptoms, the current product usage, daily treatment procedure, other daily habits, readings from bio sensors, and the like. For example, an acne breakout may be due to one or a combination of factors including hormonal changes, age, oily skin, product side affects, features in the information gathered by the vision system, and the like. The VPA system may leverage all the information to narrow down the concern and the cause.

At step 808, the VPA may determine, based on the condition/concern to be evaluated, one or more parameters for capturing images that pertain to the concern. Non-limiting examples of such parameters include the target surface (e.g., skin), the region of interest (e.g., cheek), any features or objects expected to be depicted (e.g., wrinkles, blemishes), and the like, as well as characteristic values of the parameters in the image (e.g., a threshold sharpness, a minimum color deviation for determining edges of blemishes). The parameters may vary for initial information gathering and doing the analysis based on the cause. As an example, initial acne determination may be based on the location, size, and severity of skin features. When a cause or condition is determined (e.g., oily skin), the parameters may expand to include characteristics of the cause or condition (e.g., how oily the skin is).

At step 810, the VPA may use the parameters to aid the user in capturing the necessary best-focused images, as described above. In some embodiments, the VPA may include radiometric processing routines to create a mobile phone-based system for analyzing any physical surface. The domain-configured VPA may, in addition to performing other tasks, guide the user in positioning the phone's camera, providing feedback (in the form of cues or instructions) to ensure the camera is in the right position and at the correct angle or position with respect to the physical surface for optimal image capture and analysis quality. In one embodiment of guiding the user to properly position the phone camera at different locations on the body, such as cheek, forehead, chin, etc., the VPA may announce the desired location. Starting from a reference point, the VPA may guide the user with audible beeps (e.g. faster beeps indicate the closeness to the desired location and continuous beep when the desired location is reached) and/or direct instruction (e.g. "tilt the phone down", "about an inch closer"). This is particularly useful when the user is photographing a location where he cannot see the display of the mobile device. At step 812, the VPA may obtain the best-focused image and determine that it satisfies the required parameters. In some embodiments, the processor may determine that the determined best-focused image or certain required features/objects is/are actually still blurry, or that the best-focused image does not contain the region of interest. The VPA may convey the information that the photos must be retaken, and may help the user take the photos again as described above.

In another embodiment of interacting with the user to secure the image, the VPA may incorporate context and expressed user intent in analyzing images. As an example, the user may respond to the VPA's prompt (step 802) by saying, "take the photo of the rash," indicating the user's intent that the VPA analyze a rash on the user's skin. If the user specifies his or her intent (e.g., as determined from the input in step 806) or the VPA algorithmically infers the intent based on the context (e.g., as a component of determining the capture parameters at step 808), the VPA can optimize image analysis (e.g., during verification of the best-focused image at step 812) to the intent. For example, the VPA may evaluate the best-focused image to determine whether it can detect the rash in the image. If the intent is not achieved, the VPA may deem the image capture unsuccessful and further adjust feedback to alter the position of the camera, as appropriate, for re-capture (step 810).

Once the image having the required quality level and depicting the features of interest is obtained, it can be stored and the other images discarded (step 814). The best-focused image may be analyzed by the VPA (i.e., by a processor or an image analysis engine on the mobile device or remotely connected thereto). The analysis may include a comparison of the image to historical data, such as past-collected images of the region of interest, to identify changes in the depicted features and/or textured surface. Thus, for example, the user may periodically photograph the region of interest during or after a treatment of a skin condition, and the VPA may determine the change in the skin condition over time if the historical data exists. At step 816, the VPA may determine whether there is historical data pertaining to the identified condition, region, or concern. For example, the VPA may access a data store containing previously captured images of the subject, such images identified (e.g., using metadata) by the date captured, concern addressed, region or features depicted, etc. If there is no historical data, the VPA may perform other analyses (e.g., proceeding to step 818) or simply confirm to the user that the image is stored.

If there is historical data pertaining to the concern being evaluated, at step 820 the VPA may compare the image to the historical data. For example, the VPA may perform an image comparison of the newly captured image to one or more previous images and identify differences between them. If the differences pertain to features that are relevant to the concern being evaluated (e.g., disappearance, reduction in size, or change in color of skin blemishes in the region of interest), the VPA may identify the differences as changes in the condition. The changes may identify the level of change, highlight the regions of change, may also overlay the quantitative an qualitative information. At step 822, the VPA may display the identified changes to the user. For example, the VPA may render to the display of the mobile device a side-by-side image including the previous image and the new image. Additionally or alternatively, the VPA may render an annotated version of the new image that graphically identifies the changes, and may also include text or an audio presentation describing the changes. In another embodiment, the data store accessed in step 820 may include data that enables the VPA to identify the ideal or target progress of the condition concerned, and at step 822 the VPA may present to the user an evaluation of the treatment progress compared to the ideal or target progress. In some embodiments, the ideal condition may be provided as a general reference in the relevant industry. This could include the skin composition, oiliness level, the color of the skin, and other factors. In another embodiment, the new image and/or results of the comparison (step 820) may be sent to a server, a physician's or aesthetician's mobile device, or another computing device of a human expert, who may then provide the results back to the user.

Returning to step 818, in some embodiments the VPA can analyze the skin condition to determine recommendations for procedures, medicines or other products, lifestyle changes, and other treatments for the condition concerned.

The VPA may provide the recommendations by considering the products being used, and suggest new products that could help the user's health and well-being. If historical data was analyzed, the VPA may incorporate the results of the analysis when determining the recommendations. The VPA may, at step 830, present the recommendations to the user via audio and/or video output of the mobile device. The presentation may include an explanation to the user of the data analyzed and the reasons that the recommendations are made. The system can also be a buddy that encourages the regular use of the product by providing related information.

Figure 9:
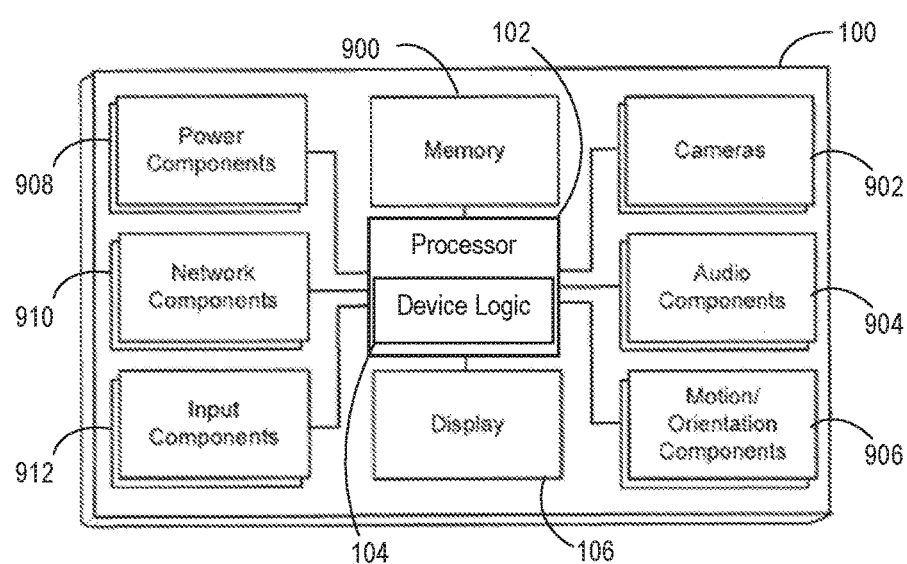
FIG. 9 is a schematic diagram of electrical components for a mobile device in accordance with the present disclosure.

FIG. 9 illustrates a logical arrangement of a set of general components of an example mobile device 100. In addition to the processor 102, the device logic 104, and the display 106 described above, the mobile device 100 may include a memory component 900, which can include many types of memory, data storage, or non-transitory computer-readable storage media, such as data stores for program instructions, images and other data, a removable memory for sharing information with other devices, etc. One or more cameras 902 or other image sensors may capture image or video content. A camera can include, or be based at least in part upon any appropriate technology, such as a CCD or CMOS image sensor having a sufficient resolution, focal range, and/or viewable area, to capture an image of the user when the user is operating the device. An image sensor can include a camera or infrared sensor that is able to image projected images or other objects in the vicinity of the device. It should be understood that image capture can be performed using a single image, multiple images, periodic imaging, continuous image capturing, image streaming, etc. Further, a device can include the ability to start and/or stop image capture, such as when receiving a command from a user, application, or other device. The mobile device 100 can similarly include at least one audio component 904, such as a mono or stereo microphone or microphone array, operable to capture audio information from at least one primary direction. A microphone can be a uni- or omni-directional microphone as known for such devices.

The mobile device 100 also can include one or more orientation and/or motion sensors 906. Such sensor(s) can include an accelerometer or gyroscope operable to detect an orientation and/or change in orientation, or an electronic or digital compass, which can indicate a direction in which the device is determined to be facing. The mechanism(s) also (or alternatively) can include or comprise a global positioning system (GPS) or similar positioning element operable to determine relative coordinates for a position of the mobile device, as well as information about relatively large movements of the device. The device can include other elements as well, such as may enable location determinations through triangulation or another such approach. These mechanisms can communicate with the processor 102, whereby the device can perform any of a number of actions such as detecting tilt as user input.

The mobile device 100 includes various power components 908 known in the art for providing power to a mobile device, which can include capacitive charging elements for use with a power pad or similar device. The mobile device can include one or more communication elements or networking sub-systems 910, such as a Wi-Fi, Bluetooth, radio frequency (RF), wired, or wireless communication system. The device in many embodiments can communicate with a network, such as the Internet, and may be able to communicate with other such devices. In some embodiments the device can include at least one additional input element 912 able to receive conventional input from a user. This conventional input can include, for example, a push button, touch pad, touchscreen, wheel, joystick, keyboard, mouse, keypad, or any other such component or element whereby a user can input a command to the device. In some embodiments, however, such a device might not include any buttons at all, and might be controlled only through a combination of visual and audio commands, such that a user can control the device without having to be in contact with the device.

The various embodiments further can be implemented in a wide variety of operating environments, which in some cases can include one or more user computers, computing devices or processing devices that can be used to operate any of a number of applications. User or client devices can include any of a number of general purpose personal computers, such as desktop, laptop or tablet computers running a standard operating system, as well as cellular, wireless and handheld devices running mobile software and capable of supporting a number of networking and messaging protocols. Such a system also can include a number of workstations running any of a variety of commercially available operating systems and other known applications for purposes such as development and database management. These devices also can include other electronic devices, such as dummy terminals, thin-clients, gaming systems and other devices capable of communicating via a network. These devices also can include virtual devices such as virtual machines, hypervisors and other virtual devices capable of communicating via a network.

Various embodiments of the present disclosure utilize a network that would be familiar to those skilled in the art for supporting communications using any of a variety of commercially-available protocols, such as Transmission Control Protocol/Internet Protocol ("TCP/IP"), User Datagram Protocol ("UDP"), protocols operating in various layers of the Open System Interconnection ("OSI") model, File Transfer Protocol ("FTP"), Universal Plug and Play ("UpnP"), Network File System ("NFS"), Common Internet File System ("CIFS") and AppleTalk. The network can be, for example, a local area network, a wide-area network, a virtual private network, the Internet, an intranet, an extranet, a public switched telephone network, an infrared network, a wireless network, a satellite network, and any combination thereof.

In embodiments utilizing a web server, the web server can run any of a variety of server or mid-tier applications, including Hypertext Transfer Protocol ("HTTP") servers, FTP servers, Common Gateway Interface ("CGI") servers, data servers, Java servers, Apache servers, and business application servers. The server(s) also may be capable of executing programs or scripts in response to requests from user devices, such as by executing one or more web applications that may be implemented as one or more scripts or programs written in any programming language, such as Java®, C, C# or C++, or any scripting language, such as Ruby, PHP, Perl, Python or TCL, as well as combinations thereof. The server(s) may also include database servers, including those commercially available from Oracle®, Microsoft®, Sybase®, and IBM® as well as open-source servers such as MySQL, Postgres, SQLite, MongoDB, and any other server capable of storing, retrieving, and accessing structured or unstructured data. Database servers may include table-based servers, document-based servers, unstructured servers, relational servers, non-relational servers or combinations of these and/or other database servers.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, a central processing unit ("CPU" or "processor"), an input device (e.g., a mouse, keyboard, controller, touch screen or keypad), and an output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a wireless or wired network card, an infrared communication device, etc.), and working memory as described above. The computer-readable storage media reader can be connected with, or configured to receive, a computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within a working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Storage media and computer readable media for containing code, or portions of code, can include any appropriate media known or used in the art, including storage media and communication media, such as, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided, a person of ordinary skill in the art will appreciate other ways and/or methods to implement the various embodiments.

Additional Examples

Illustrative examples of the technologies disclosed herein are provided below. An embodiment of the technologies may include any one or more, and any combination of, the examples described below.

In an example 1, a method of capturing, using a mobile device, a best-focused image of a skin surface of a subject comprises setting a camera of the mobile device to a fixed focal length, capturing, using the camera, a current image of a plurality of images of the skin surface, the plurality of images having a sequence and including a first previous image captured, using the camera, immediately previously to the current image and a second previous image captured, using the camera, immediately previously to the first previous image, producing a grayscale image from the current image, transforming the grayscale image, using a Laplacian pyramid, to produce a plurality of first luminance values from the grayscale image and a plurality of second luminance values from the plurality of first luminance values, averaging a plurality of first squared values, each comprising a square of a corresponding first luminance value of the plurality of first luminance values, to produce a first energy value, averaging a plurality of second squared values, each comprising a square of a corresponding second luminance value of the plurality of second luminance values, to produce a second energy value, calculating a first ratio of the first energy value to the second energy value, calculating, as an average first energy value of the first previous image, an average of the first energy value, a corresponding first energy value of the first previous image, and a corresponding first energy value of the second previous image, calculating, as an average first ratio of the first previous image, an average of the first ratio, a corresponding first ratio of the first previous image, and a corresponding first ratio of the second previous image, determining that the first previous image is one of a plurality of valid images, wherein each valid image of the plurality of valid images is an image of the plurality of images and has a corresponding average first energy value above an energy threshold value and a corresponding average first ratio approximately equal to 1.0, determining that a first valid image of the plurality of valid images is the best-focused image, wherein the first valid image has a corresponding average first energy value that is greater than the corresponding average first energy values of a previous valid image captured immediately before the first valid image and a subsequent valid image captured immediately after the first valid image, and performing an action associated with the best-focused image.

An example 2 includes the subject matter of example 1, wherein capturing the current image comprises automatically capturing the plurality of images at a capture rate as the mobile device is continuously moved between a first point that is a first distance away from the skin surface and a second point that is a second distance away from the skin surface, the first distance being less than the focal length and the second distance being greater than the focal length and wherein performing the action comprises stopping the capturing of the plurality of images, such that the current image is the last captured image of the plurality of images, the method further comprising, before determining the best-focused image, determining that the plurality of valid images includes at least a minimum number of the plurality of images.

An example 3 includes the subject matter of any of examples 1 and/or 2, wherein the skin surface is located such that a display of the mobile device is not viewable by the subject while the subject is moving the mobile device during capture of the plurality of images, and capturing the plurality of images comprises determining, using an accelerometer of the mobile device, that a speed at which the mobile device is being moved exceeds a predetermined speed limit and producing, using the mobile device, an audible alert that indicates to the subject to slow movement of the mobile device, wherein performing the action further comprises producing, using the mobile device, an audible indication that the best-focused image has been captured.

An example 4 includes the subject matter of any of examples 1, 2, and/or 3, wherein the method further includes the steps of further transforming the grayscale image, using the Laplacian pyramid, to produce a plurality of third luminance values from the plurality of second luminance values, averaging a plurality of third squared values, each comprising a square of a corresponding third luminance value of the plurality of third luminance values, to produce a third energy value, calculating a second ratio of the first energy value to the third energy value, calculating, as an average second energy value of the first previous image, an average of the second energy value, a corresponding second energy value of the first previous image, and a corresponding second energy value of the second previous image, calculating, as an average third energy value of the first previous image, an average of the third energy value, a corresponding third energy value of the first previous image, and a corresponding third energy value of the second previous image, and calculating, as an average second ratio of the first previous image, an average of the second ratio, a corresponding second ratio of the first previous image, and a corresponding second ratio of the second previous image, wherein each valid image of the plurality of valid images further has a corresponding average second energy value and a corresponding average third energy value both above the energy threshold value and a corresponding average second ratio approximately equal to 1.0.

In an example 5, a method of determining, using a mobile device, a best-focused image of a textured surface comprises receiving a plurality of images of the textured surface, the plurality of images captured by a camera of the mobile device while the camera is set to a fixed focal length, applying a Laplacian pyramid to a first image of the plurality of images to generate a Laplacian pyramid having a first level based on the first image and a second level based on the first level, determining a first energy value of the first image, the first energy value representing a Laplacian energy of the first level, determining a second energy value of the first image, the second energy value representing a Laplacian energy of the second level, determining that the first energy value exceeds an energy threshold and is approximately equal to the second energy value, determining, based at least in part on the first energy value of the first image and a corresponding first energy value of each valid image of a plurality of valid images, that the first image is the best-focused image, the plurality of valid images comprising all of the plurality of images having a corresponding first energy value that exceeds the energy threshold and is approximately equal to a corresponding second energy value, and performing an action associated with the best-focused image.

An example 6 includes the subject matter of example 5, wherein receiving the plurality of images comprises controlling the camera to capture the plurality of images at a capture rate as the mobile device is continuously moved between a first point that is a first distance away from the textured surface and a second point that is a second distance away from the textured surface, the first distance being less than the focal length and the second distance being greater than the focal length.

An example 7 includes the subject matter of an of examples 5 and/or 6, wherein receiving the plurality of images further comprises determining one or more conditions of the mobile device and producing, using the mobile device, one or more audible cues based on the one or more conditions, the one or more audible cues aiding a user of the mobile device to position the mobile device for capturing one or more of the plurality of images.

An example 8 includes the subject matter of any of examples 5, 6, and/or 7, wherein determining the one or more conditions comprises determining, using an accelerometer of the mobile device, that a speed at which the mobile device is being moved exceeds a predetermined speed limit and wherein producing the one or more audible cues comprises producing an audible alert that indicates to the user to slow movement of the mobile device.

An example 9 includes the subject matter of any of examples 5, 6, 7, and/or 8, wherein the plurality of images includes a current image captured immediately subsequently to the first image, and wherein performing the action comprises controlling the camera to stop capturing the plurality of images such that the current image is captured last of the plurality of images.

An example 10 includes the subject matter of any of examples 5, 6, 7, 8, and/or 9, wherein determining that the first image is the best-focused image comprises calculating an average first energy value from corresponding first energy values of the first image, the current image, and a previous image of the plurality of images, the previous image being captured immediately previously to the first image, calculating an average first ratio from of a plurality of first ratios, each associated with a corresponding image of the plurality of images and comparing a corresponding first energy value of the image to a corresponding second energy value of the image, the plurality of first ratios including a corresponding first ratio for each of the first image, the previous image, and the current image, determining that the average first energy value exceeds the energy threshold and the average first ratio is approximately 1.0, and determining that the average first energy value of the first image is greater than a corresponding average first energy value of each of a previous valid image of the plurality of valid images, the previous valid image captured immediately before the first image and a subsequent valid image of the plurality of valid images, the subsequent valid image captured immediately after the first image.

An example 11 includes the subject matter of any of examples 5, 6, 7, 8, 9, and/or 10, wherein applying the Laplacian pyramid comprises selecting one or more parameters of the Laplacian pyramid such that a first Laplacian pyramid based on a first unfocused image captured when the mobile device is a first distance away from the textured surface, the first distance being less than the focal length, exhibits a corresponding first level and a corresponding second level in which a Laplacian energy of the first level is higher than and not approximately equal to a Laplacian energy of second level and a second Laplacian pyramid based on a second unfocused image captured when the mobile device is a second distance away from the textured surface, the second distance being greater than the focal length, exhibits a corresponding first level in which a Laplacian energy of the first level does not exceed the energy threshold.

An example 12 includes the subject matter of any of examples 5, 6, 7, 8, 9, 10, and/or 11, wherein performing the action comprises determining that a blurriness of the first image exceeds a threshold blurriness and producing, using the mobile device, a cue indicating that the plurality of images should be discarded and a plurality of new images of the textured surface must be captured.

An example 13 includes the subject matter of any of examples 5, 6, 7, 8, 9, 10, 11, and/or 12, wherein the textured surface is a skin surface of a subject, the skin surface having a base appearance and one or more weak features that each are not significantly differentiated from the base appearance or from the other one or more weak features, and wherein performing the action comprises detecting the one or more weak features in the best-focused image and generating information about the one or more weak features.

An example 14 includes the subject matter of any of examples 5, 6, 7, 8, 9, 10, 11, 12, and/or 13, wherein the one or more weak features are selected from the group comprising furrows, wrinkles, and pores.

In an example 15, a mobile device comprises a camera set to a focal length, memory storing device logic and a Laplacian pyramid, and a processor in electronic communication with the memory and the camera, the processor executing the device logic to receive, from the camera, a plurality of images of a region of interest, apply the discrete Laplace operator to each image to generate a corresponding Laplacian pyramid having a first level based on the image and a second level based on the first level, determine, for each image of the plurality of images, a corresponding first energy value representing Laplacian energy of the first level of the corresponding pyramid, determine, for each image of the plurality of images, a corresponding second energy value representing Laplacian energy of the second level of the corresponding pyramid, determine a best-focused image of the plurality of images based at least in part on the corresponding first energy value of each valid image of a plurality of valid images including the best-focused image, wherein each valid image of the plurality of valid images is one of the plurality of images and has a first energy value that exceeds an energy threshold and is approximately equal to a second energy value, and perform an action based on the best-focused image.

An example 16 includes the subject matter of example 15, wherein the discrete Laplace operator comprises a high-pass filtering kernel of a predetermined size and a predetermined frequency, the predetermined size and the predetermined frequency selected such that a first Laplacian pyramid for a first unfocused image captured when the mobile device is a first distance away from a subject, the first distance being less than the focal length, exhibits a corresponding first level and a corresponding second level in which a Laplacian energy of the first level is higher than and not approximately equal to a Laplacian energy of second level and a second Laplacian pyramid based on a second unfocused image captured when the mobile device is a second distance away from the subject, the second distance being greater than the focal length, exhibits a corresponding first level in which a Laplacian energy of the first level does not exceed the energy threshold.

An example 17 includes the subject matter of any of examples 15 and/or 16, further comprising an autofocus motor, wherein the focal length of the camera is adjustable by the autofocus motor from a minimum focal length to a maximum focal length, and wherein to receive the plurality of images, the processor executes the device logic to fix the focal length at the minimum focal length, and to disable the autofocus motor, during capture by the camera of the plurality of images.

An example 18, includes the subject matter of any of examples 15, 16, and/or 17, further comprising a range sensor in electronic communication with the processor, wherein the region of interest includes a textured surface and to receive the plurality of images, the processor executes the device logic to receive a signal from the range sensor, determine that the signal indicates that the range sensor detected that the mobile device is positioned at a first point that is a first distance away from the textured surface, the first distance being less than the focal length, and control the camera to capture the plurality of images at a capture rate as the mobile device is continuously moved from the first point to a second point that is a second distance away from the textured surface, the second distance being greater than the focal length.

An example 19, includes the subject matter of any of examples 15, 16, 17, and/or 18, wherein the processor receives each image of the plurality of images as the image is captured, such that the plurality of images has a first sequence and the plurality of valid images has a second sequence comprising the first sequence with each image of the plurality of images that is not one of the plurality of valid images removed and wherein each valid image of the plurality of valid images further has a corresponding average first energy value and a corresponding average second energy value that exceed the energy threshold and are approximately equal, the processor executing the device logic to calculate the corresponding average first energy value from the corresponding first energy values of the valid image, a previous image positioned immediately before the valid image in the first sequence, and a subsequent image positioned immediately after the valid image in the first sequence, calculate the corresponding average second energy value from the corresponding second energy values of the valid image, the previous image, and the subsequent image and determine that the corresponding average first energy value exceeds the energy threshold and is approximately equal to the corresponding average second energy value, wherein to determine the best-focused image, the processor executes the device logic to determine that the corresponding average first energy value of a first image of the plurality of valid images is greater than the corresponding average first energy value of each of a previous valid image of the plurality of valid images, the previous valid image positioned immediately before the first image in the second sequence and a subsequent valid image of the plurality of valid images, the subsequent valid image positioned immediately after the first image in the second sequence, wherein to perform the action, the processor executes the device logic to control the camera to stop capturing the plurality of images.

An example 20, includes the subject matter of any of examples 15, 16, 17, 18, and/or 19, further comprising a speaker, wherein to receive the plurality of images, the processor executes the device logic to determine one or more conditions of the mobile device, generate one or more audible cues based on the one or more conditions, the one or more audible cues aiding a user of the mobile device to position the mobile device for capturing one or more of the plurality of images, and output the one or more audible cues via the speaker.

What is claimed is:

1. A method of capturing, using a mobile device, a best-focused image of a skin surface of a subject, the method comprising:

setting a camera of the mobile device to a fixed focal length;

capturing, using the camera, a current image of a plurality of images of the skin surface, the plurality of images having a sequence and including a first previous image captured, using the camera, previously to the current image and a second previous image captured, using the camera, previously to the first previous image;

producing a modified image from the current image;

transforming the modified image, using a Laplacian pyramid, to produce a plurality of first luminance values from the modified image and a plurality of second luminance values from the plurality of first luminance values;

averaging a plurality of first squared values, each comprising a square of a corresponding first luminance value of the plurality of first luminance values, to produce a first energy value;

averaging a plurality of second squared values, each comprising a square of a corresponding second luminance value of the plurality of second luminance values, to produce a second energy value;

calculating a first ratio of the first energy value to the second energy value;

calculating, as an average first energy value of the first previous image, an average of the first energy value, a corresponding first energy value of the first previous image, and a corresponding first energy value of the second previous image;

calculating, as an average first ratio of the first previous image, an average of the first ratio, a corresponding first ratio of the first previous image, and a corresponding first ratio of the second previous image;

determining that the first previous image is one of a plurality of valid images, wherein each valid image of the plurality of valid images is an image of the plurality of images and has:

a corresponding average first energy value above an energy threshold value; and a corresponding average first ratio approximately equal to 1.0;

determining that a first valid image of the plurality of valid images is the best-focused image, wherein the first valid image has a corresponding average first energy value that is greater than the corresponding average first energy values of:

a previous valid image captured immediately before the first valid image; and a subsequent valid image captured immediately after the first valid image; and performing an action associated with the best-focused image.

2. The method of claim 1, wherein capturing the current image comprises automatically capturing the plurality of images at a capture rate as the mobile device is continuously moved between a first point that is a first distance away from the skin surface and a second point that is a second distance away from the skin surface, the first distance being less than the fixed focal length and the second distance being greater than the fixed focal length; and wherein performing the action comprises stopping the capturing of the plurality of images, such that the current image is a last captured image of the plurality of images;

the method further comprising, before determining the best-focused image, determining that the plurality of valid images includes at least a minimum number of the plurality of images.

3. The method of claim 2, wherein the skin surface is located such that a display of the mobile device is not viewable by the subject while the subject is moving the mobile device during capture of the plurality of images, and capturing the plurality of images comprises:

determining, using an accelerometer of the mobile device, that a speed at which the mobile device is being moved exceeds a predetermined speed limit; and producing, using the mobile device, an audible alert that indicates to the subject to slow movement of the mobile device; and wherein performing the action further comprises producing, using the mobile device, an audible indication that the best-focused image has been captured.

4. The method of claim 1, further comprising:

further transforming the modified image, using the Laplacian pyramid, to produce a plurality of third luminance values from the plurality of second luminance values;

averaging a plurality of third squared values, each comprising a square of a corresponding third luminance value of the plurality of third luminance values, to produce a third energy value;

calculating a second ratio of the first energy value to the third energy value;

calculating, as an average second energy value of the first previous image, an average of the second energy value, a corresponding second energy value of the first previous image, and a corresponding second energy value of the second previous image;

calculating, as an average third energy value of the first previous image, an average of the third energy value, a corresponding third energy value of the first previous image, and a corresponding third energy value of the second previous image; and calculating, as an average second ratio of the first previous image, an average of the second ratio, a corresponding second ratio of the first previous image, and a corresponding second ratio of the second previous image;

wherein each valid image of the plurality of valid images further has:

a corresponding average second energy value and a corresponding average third energy value both above the energy threshold value; and a corresponding average second ratio approximately equal to 1.0.

5. A method of determining, using a mobile device, a best-focused image of a textured surface, the method comprising:

receiving a plurality of images of the textured surface, the plurality of images captured by a camera of the mobile device while the camera is set to a focal length;

applying a Laplacian pyramid to a first image of the plurality of images to generate a Laplacian pyramid having a first level based on the first image and a second level based on the first level;

determining a first energy value of the first image, the first energy value representing a Laplacian energy of the first level;

determining a second energy value of the first image, the second energy value representing a Laplacian energy of the second level;

determining that the first energy value exceeds an energy threshold and is approximately equal to the second energy value;

determining, based at least in part on the first energy value of the first image and a corresponding first energy value of each valid image of a plurality of valid images, that the first image is the best-focused image, the plurality of valid images comprising all of the plurality of images having a corresponding first energy value that exceeds the energy threshold and is approximately equal to a corresponding second energy value; and performing an action associated with the best-focused image;

wherein receiving the plurality of images comprises controlling the camera to capture the plurality of images at a capture rate as the mobile device is continuously moved between a first point that is a first distance away from the textured surface and a second point that is a second distance away from the textured surface, the first distance being less than the focal length and the second distance being greater than the focal length;

wherein the plurality of images includes a current image captured immediately subsequently to the first image, and wherein performing the action comprises controlling the camera to stop capturing the plurality of images such that the current image is captured last of the plurality of images;

wherein determining that the first image is the best-focused image comprises:

calculating an average first energy value from corresponding first energy values of the first image, the current image, and a previous image of the plurality of images, the previous image being captured immediately previously to the first image;

calculating an average first ratio from of a plurality of first ratios, each associated with a corresponding image of the plurality of images and comparing a corresponding first energy value of the image to a corresponding second energy value of the image, the plurality of first ratios including a corresponding first ratio for each of the first image, the previous image, and the current image;

determining that the average first energy value exceeds the energy threshold and the average first ratio is approximately 1.0;

determining that the average first energy value of the first image is greater than a corresponding average first energy value of each of:

a previous valid image of the plurality of valid images, the previous valid image captured immediately before the first image; and a subsequent valid image of the plurality of valid images, the subsequent valid image captured immediately after the first image.

6. The method of claim 5, wherein receiving the plurality of images further comprises: determining one or more conditions of the mobile device; and producing, using the mobile device, one or more audible cues based on the one or more conditions, the one or more audible cues aiding a user of the mobile device to position the mobile device for capturing one or more of the plurality of images.

7. The method of claim 6, wherein determining the one or more conditions comprises determining, using an accelerometer of the mobile device, that a speed at which the mobile device is being moved exceeds a predetermined speed limit; and wherein producing the one or more audible cues comprises producing an audible alert that indicates to the user to slow movement of the mobile device.

8. The method of claim 5, wherein applying the Laplacian pyramid comprises selecting one or more parameters of the Laplacian pyramid such that:

a first Laplacian pyramid based on a first unfocused image captured when the mobile device is a first distance away from the textured surface, the first distance being less than the focal length, exhibits a corresponding first level and a corresponding second level in which a Laplacian energy of the first level is higher than and not approximately equal to a Laplacian energy of second level; and a second Laplacian pyramid based on a second unfocused image captured when the mobile device is a second distance away from the textured surface, the second distance being greater than the focal length, exhibits a corresponding first level in which a Laplacian energy of the first level does not exceed the energy threshold.

9. The method of claim 5, wherein performing the action comprises:

determining that a blurriness of the first image exceeds a threshold blurriness; and producing, using the mobile device, a cue indicating that the plurality of images should be discarded and a plurality of new images of the textured surface must be captured.

10. The method of claim 5, wherein the textured surface is a skin surface of a subject, the skin surface having a base appearance and one or more weak features that each are not significantly differentiated from the base appearance or from one or more other weak features, and wherein performing the action comprises detecting the one or more weak features in the best-focused image and generating information about the one or more weak features.

11. The method of claim 10, wherein the one or more weak features are selected from a group comprising furrows, wrinkles, and pores.

12. A mobile device comprising:

a camera set to a focal length;

memory storing device logic and a Laplacian pyramid; and a processor in electronic communication with the memory and the camera, the processor executing the device logic to:

receive, from the camera, a plurality of images of a region of interest;

apply the Laplacian pyramid to each image to generate a corresponding Laplacian pyramid having a first level based on the image and a second level based on the first level;

determine, for each image of the plurality of images, a corresponding first energy value representing Laplacian energy of the first level of the corresponding Laplacian pyramid;

determine, for each image of the plurality of images, a corresponding second energy value representing Laplacian energy of the second level of the corresponding Laplacian pyramid;

determine a best-focused image of the plurality of images based at least in part on the corresponding first energy value of each valid image of a plurality of valid images including the best-focused image, wherein each valid image of the plurality of valid images is one of the plurality of images and has a first energy value that exceeds an energy threshold and is approximately equal to a second energy value; and perform an action based on the best-focused image;

a range sensor in electronic communication with the processor, wherein the region of interest includes a textured surface and to receive the plurality of images, the processor executes the device logic to:

receive a signal from the range sensor;

determine that the signal indicates that the range sensor detected that the mobile device is positioned at a first point that is a first distance away from the textured surface, the first distance being less than the focal length; and control the camera to capture the plurality of images at a capture rate as the mobile device is continuously moved from the first point to a second point that is a second distance away from the textured surface, the second distance being greater than the focal length;

wherein the processor receives each image of the plurality of images as the image is captured, such that the plurality of images has a first sequence and the plurality of valid images has a second sequence comprising the first sequence with each image of the plurality of images that is not one of the plurality of valid images removed;

wherein each valid image of the plurality of valid images further has a corresponding average first energy value and a corresponding average second energy value that exceed the energy threshold and are approximately equal, the processor executing the device logic to:

calculate the corresponding average first energy value from the corresponding first energy values of the valid image, a previous image positioned immediately before the valid image in the first sequence, and a subsequent image positioned immediately after the valid image in the first sequence;

calculate the corresponding average second energy value from the corresponding second energy values of the valid image, the previous image, and the subsequent image; and determine that the corresponding average first energy value exceeds the energy threshold and is approximately equal to the corresponding average second energy value; wherein to determine the best-focused image, the processor executes the device logic to:

determine that the corresponding average first energy value of a first image of the plurality of valid images is greater than the corresponding average first energy value of each of:

a previous valid image of the plurality of valid images, the previous valid image positioned immediately before the first image in the second sequence; and a subsequent valid image of the plurality of valid images, the subsequent valid image positioned immediately after the first image in the second sequence; and wherein to perform the action, the processor executes the device logic to control the camera to stop capturing the plurality of images.

13. The mobile device of claim 12, wherein the Laplacian pyramid comprises a high-pass filtering kernel of a predetermined size and a predetermined frequency, the predetermined size and the predetermined frequency selected such that:

a first Laplacian pyramid for a first unfocused image captured when the mobile device is a first distance away from a subject, the first distance being less than the focal length, exhibits a corresponding first level and a corresponding second level in which a Laplacian energy of the first level is higher than and not approximately equal to a Laplacian energy of second level; and a second Laplacian pyramid based on a second unfocused image captured when the mobile device is a second distance away from the subject, the second distance being greater than the focal length, exhibits a corresponding first level in which a Laplacian energy of the first level does not exceed the energy threshold.

14. The mobile device of claim 12, further comprising an autofocus motor, wherein the focal length of the camera is adjustable by the autofocus motor from a minimum focal length to a maximum focal length, and wherein to receive the plurality of images, the processor executes the device logic to fix the focal length at the minimum focal length, and to disable the autofocus motor, during capture by the camera of the plurality of images.

15. The mobile device of claim 12, further comprising a speaker, wherein to receive the plurality of images, the processor executes the device logic to:

determine one or more conditions of the mobile device; and generate one or more audible cues based on one or more conditions, the one or more audible cues aiding a user of the mobile device to position the mobile device for capturing one or more of the plurality of images; and output the one or more audible cues via the speaker.

* * * * *